(12) United States Patent
Pilz et al.

(10) Patent No.: US 9,757,019 B2
(45) Date of Patent: Sep. 12, 2017

(54) OPTICAL MEDICAL INSTRUMENT

(71) Applicant: Karl Storz GmbH & Co. KG, Tuttlingen (DE)

(72) Inventors: Kevin Pilz, Tuttlingen (DE); Markus Kupferschmid, Emmingen-Liptingen (DE); Daniel Ulmschneider, Nendingen (DE); Andreas Heni, Fridingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 220 days.

(21) Appl. No.: 14/720,252

(22) Filed: May 22, 2015

(65) Prior Publication Data

US 2015/0335233 A1    Nov. 26, 2015

(30) Foreign Application Priority Data

May 22, 2014   (DE) .................. 10 2014 107 205

(51) Int. Cl.
*A61B 1/12*    (2006.01)
*A61B 1/00*    (2006.01)
*A61B 1/06*    (2006.01)
*G02B 23/24*   (2006.01)

(52) U.S. Cl.
CPC .......... *A61B 1/128* (2013.01); *A61B 1/00071* (2013.01); *A61B 1/00128* (2013.01); *A61B 1/0676* (2013.01); *G02B 23/2476* (2013.01); *A61B 1/0684* (2013.01); *G02B 23/2461* (2013.01)

(58) Field of Classification Search
CPC ... A61B 1/128; A61B 1/00071; A61B 1/0676; A61B 1/00128; A61B 1/0684; G02B 23/2476; G02B 23/2461
See application file for complete search history.

(56) References Cited

U.S. PATENT DOCUMENTS

| 5,207,674 A | 5/1993 | Hamilton |
| 2006/0195165 A1 | 8/2006 | Gertner et al. |
| 2008/0151046 A1 | 6/2008 | Scott et al. |
| 2011/0306834 A1 | 12/2011 | Schrader et al. |

FOREIGN PATENT DOCUMENTS

| DE | 102010024003 A1 | 12/2011 |
| JP | 2009011612 A | 1/2009 |

OTHER PUBLICATIONS

European Examination Report Application No. 15167503.0 Completed Date: Nov. 24, 2016 3 Pages.
European Search Report Application No. EP 15167503.0 Completed: Oct. 1, 2015; Mailing Date: Oct. 12, 2015 6 pages.

*Primary Examiner* — Rex R Holmes
(74) *Attorney, Agent, or Firm* — Whitmyer IP Group LLC

(57) ABSTRACT

An optical medical instrument, in particular an endoscope or exoscope, has an elongate tubular shaft, a heat source generating lost heat, and a heat pipe which extends inside the shaft, in the longitudinal direction of the shaft, and has a distal heat pipe end and a proximal heat pipe end, wherein the heat pipe is thermally coupled to the heat source in order to collect heat from the latter and remove the heat from the heat source. Between the distal heat pipe end and the proximal heat pipe end, the heat pipe is coupled thermally conductively and two-dimensionally to the shaft over at least a partial length of the heat pipe and over at least a partial circumference of the heat pipe, in order to remove heat from the heat pipe, over at least a partial length and over at least a partial circumference of the shaft, to the environment.

20 Claims, 16 Drawing Sheets

OPTICAL MEDICAL INSTRUMENT

CROSS REFERENCE TO RELATED APPLICATIONS

The present application claims priority of German patent application No. 10 2014 107 205.7 filed on May 22, 2014, the whole contents of which is incorporated herein by reference.

BACKGROUND OF THE INVENTION

The invention relates to an optical medical instrument, in particular an endoscope or exoscope. In particular, the invention relates to an optical medical instrument of the type comprising an elongate tubular shaft, a heat source generating lost heat, a heat pipe extending inside the shaft in the longitudinal direction of the shaft and having a distal heat pipe end and a proximal heat pipe end, wherein the heat pipe is thermally coupled to the heat source in order to collect heat from the latter and remove the heat from the heat source.

Endoscopes are used in the context of minimally invasive surgery as viewing instruments. The elongate shaft of an endoscope is inserted partially into the body through an artificially created or natural opening.

An exoscope is a viewing instrument which is used for imaging in open surgery. An exoscope is placed completely outside the body, at a distance from the operating site, by means of a holding arm.

Nowadays, endoscopes and exoscopes are often designed as video endoscopes and video exosopes,respectively, and are accordingly equipped with electronic components such as image sensors, control electronics for the image sensors and/or light sources such as LEDs for lighting. During operation, the electronic components generate lost heat and thus constitute one or more heat sources. The lost heat has to be removed from the one or more heat sources via a heat transfer to the environment. The removal of the heat is necessary to protect the electronic components from overheating and from resulting loss of performance and even damage. Moreover, in the case of an endoscope, at least the portion of the shaft inserted into the body must not heat to such an extent that there is a risk of causing patient injuries. An endoscope used in surgery is subject to the provisions of the Medical Devices Act. According to the Medical Devices Act, the outside of the endoscope shaft must not exceed a temperature of 41° C., so as to avoid heat-induced damage to tissue in the human or animal body.

Without a dedicated heat removal management system, the heat transfer from the heat source to the environment takes place by free convection or thermal radiation. For this heat transfer, the surface of the instrument is available as an interface to the environment. However, as a result of the local position of the heat source or heat sources, the surface is not uniformly heated. Local temperature maxima and minima occur. Therefore, the surface of the instrument is not integrated uniformly in the process of heat removal to the environment. In particular, the locations of the temperature maxima furthermore exceed the permissible temperatures, while the potential of the temperature minima remains unused. In view of the increased use of high-performance electronics in optical medical instruments such as endoscopes and exoscopes, this localized heat transfer will in future be no longer sufficient to adequately cool the electronics.

A further disadvantage lies in a high temperature gradient, which results from the uneven heat transfer to the environment, i.e. a high temperature difference between heat source and environment. The high temperatures at the heat source, i.e. the electronics, have a negative effect on the performance of the electronics.

In the document DE 10 2010 024 003 A1, an endoscope is described that has a heat pipe through which the lost heat generated by a light source arranged in the distal area of the shaft is dissipated in the proximal direction, wherein the heat pipe extends as far as a headpiece at the proximal end of the shaft, wherein a heat sink body is arranged in the headpiece, which heat sink body is thermally coupled to the heat pipe, collects the lost heat from the heat pipe and releases it to the environment either directly or via the housing of the headpiece. In order to avoid a situation where the distal end of the shaft heats to a temperature above the maximum permissible temperature of 41° C., provision is further made that the shaft is thermally insulated on the inside from the heat pipe.

If the heat source is a powerful electronics unit that generates a lot of lost heat, this heat removal management system of the known endoscope is of limited use and, in particular if the heat source is located in the distal area of the shaft, does not ensure adequate removal of heat from the heat source.

Moreover, US 2008/0151046 A1 describes an endoscope in which, in order to remove lost heat from a light source arranged in the distal area of the shaft, a heat pipe is present that extends in the proximal direction from the distal light source, to which the heat pipe is thermally coupled, along a short partial length of the shaft, wherein a heat-conducting wire, for example a copper wire, is connected to the proximal end of the heat pipe, wherein the wire extends farther in the proximal direction and has its proximal end connected thermally conductively to the inner face of the shaft of the endoscope. The heat is transferred to the endoscope shaft only in punctiform fashion via the end of the wire, as a result of which the heat removal to the environment likewise only takes place in punctiform fashion, which represents an inadequate removal of heat in cases where there are considerable amounts of heat present.

SUMMARY OF THE INVENTION

It is an object of the invention to provide an optical medical instrument in which the removal of lost heat to the environment of the instrument is improved.

According to an aspect of the invention, an optical medical instrument is provided, comprising an elongate tubular shaft, a heat source generating lost heat, a heat pipe extending inside the shaft in the longitudinal direction of the shaft and having a distal heat pipe end and a proximal heat pipe end, the heat pipe being thermally coupled to the heat source in order to collect heat from the heat source and to remove the heat from the heat source, wherein the heat pipe is coupled thermally conductively and two-dimensionally to the shaft between the distal heat pipe end and the proximal heat pipe end over at least a partial length of the heat pipe and over at least a partial circumference of the heat pipe, in order to remove heat from the heat pipe, over at least a partial length and over at least a partial circumference of the shaft, to the environment.

In contrast to the prior art, the present invention uses the shaft of the instrument for heat transfer to the environment, and not just in punctiform fashion, but over a large surface area. Therefore, in the instrument according to the invention, the shaft of the instrument itself is used as a heat sink.

Moreover, in the prior art, it was assumed that a heat pipe can only collect heat at one end and release heat at the opposite end. However, in the context of the invention, it has been found that a heat pipe can also release heat between its two ends. If, as is provided for according to the invention, the whole shaft of the instrument, or at least a large area of the shaft, is used as a heat sink, the heat dissipated from the heat source will be released by the heat pipe precisely at the location where the shaft is at its coldest. The greater the area and the surface of the thermally conductive coupling between the heat pipe and the shaft, the greater the number of places at which the heat sink can be located along the heat pipe and the shaft, sometimes all the way along the heat pipe. Therefore, according to the function of the heat pipes, the position of the heat sink is automatically established "flexibly" along the shaft. This concept according to the invention is referred to hereinbelow as a "flexible heat sink". The concept of the "flexible heat sink" ensures that the heat is distributed relatively uniformly across the existing surface of the shaft and, as a result, temperature differences are kept as low as possible. Advantageously, local temperature peaks and therefore high temperature gradients along the shaft are at least reduced or even avoided in this way. The lost heat is instead transferred uniformly from the heat pipe to the shaft and from the latter to the environment. The danger of the shaft heating to a temperature above the maximum limit of 41° C. allowed by the Medical Devices Act is therefore likewise avoided. The heat removal in the instrument according to the invention is also very efficient, since the heat transfer takes place across a large surface area of the shaft.

It will be appreciated that the shaft of the instrument according to the invention is not thermally insulated from the heat pipe on the inside but instead, on the contrary, is coupled to the heat pipe in a way that provides the best possible thermal conductivity. The shaft itself is thermally conductive, i.e. comprises a thermally conductive material, e.g. stainless steel. Likewise, the heat pipe has no insulation on the outside and can in particular be a tube made of a material with good heat conduction, for example copper or aluminum.

In a preferred embodiment, within the meaning of the aforementioned "flexible heat sink", the heat pipe is coupled thermally conductively to the shaft over at least half the total length of the heat pipe, and, more preferably, the heat pipe is coupled thermally conductively to the shaft almost or completely over the total length of the heat pipe.

Moreover, within the principle of the "flexible heat sink", and for the purpose of a still further improved and more uniform heat transfer from the heat pipe to the shaft, the heat pipe preferably extends over at least half the length of the shaft and is coupled thermally conductively to the shaft over at least half the length of the shaft.

If the available space in the shaft of the instrument so permits, it is optimal if the heat pipe or an arrangement of several heat pipes extends over considerably more than half the length of the shaft, preferably over more than three quarters of the length of the shaft, and is coupled thermally conductively to the shaft along this area.

Instead of a single, long continuous heat pipe, the heat pipe can also have at least two heat pipes which are arranged one behind the other in the longitudinal direction of the shaft, if appropriate with a partial overlap and/or with a thermally conductive coupling to each other.

The heat pipe can be thermally coupled at least in part directly to the shaft, wherein the heat pipe preferably is in form-fit contact with an inner face of the shaft over at least part of the circumference, as is provided for in a preferred embodiment, and/or the heat pipe can be coupled thermally conductively to the shaft at least over part of the circumference via a heat sink body, wherein the heat sink body is in contact with the heat pipe and with an inner face of the shaft, in each case with a form fit around at least part of the circumference, as is provided for in another preferred embodiment.

An important factor regarding the efficacy of the heat removal management system according to the invention is the thermally conductive connection of the heat pipe to the shaft over a surface area that is as large as possible, whether it be the direct connection of the heat pipe to the inner face of the shaft or, alternatively or in addition, the connection via one or more heat sink bodies. The form fit between the heat pipe and the inner face of the shaft in a direct thermally conductive coupling and the form fit between the heat sink body and the heat pipe, on the one hand, and between the heat sink body and the inner face of the shaft, on the other hand, in the case of an indirect thermally conductive coupling of the heat pipe to the shaft, improve the thermal connection of the heat pipe to the shaft.

With regard to the indirect thermally conductive connection of the heat pipe to the shaft, it is also preferable if the heat pipe is coupled thermally conductively to the shaft via a plurality of heat sink bodies at least partially about the circumference, wherein the heat sink bodies are distributed along the heat pipe.

In another preferred embodiment, the heat pipe is connected to the heat source via a thermally conductive heat coupling element, to which the heat pipe is preferably connected with a form fit.

Compared to a coupling between heat pipe and heat source based on heat radiation or convection, the thermally conductive coupling has the advantage of a more effective heat transfer from the heat source to the heat pipe, particularly if the connection of the heat pipe to the heat coupling element is made with a form fit.

Regarding the aforementioned embodiment, it is preferable if the heat pipe is pressed into the heat coupling element.

By pressing the heat pipe into the heat coupling element, a form fit connection between the heat pipe and the heat coupling element is produced in a simple manner, and the heat pipe can also be deformed in cross section by being pressed in.

To avoid an excessive deformation of the heat pipe, which can impair the inner capillary action of the heat pipe, the form-fit connection of the heat pipe to the heat coupling element can also be additionally fixed by means of a thermally conductive joining material.

In this case, the form-fit connection of the heat pipe to the heat coupling element is made with a clearance fit, wherein the free space created by the fit clearance and the remaining degrees of freedom are compensated by the additional joining, for example gluing or soldering. However, the additional cohesive connection is dispensed with if the thermal expansion behaviour of the heat coupling element or of the heat pipe has to be taken into consideration by providing corresponding remaining degrees of freedom.

According to another preferred embodiment, it is likewise possible that the heat coupling element is designed as a thermally conductive bearing with at least one degree of freedom of movement with respect to the heat source.

This measure is advantageous particularly if the heat source is a movable heat source, for example a pivotably mounted image sensor in the case of a pivotable camera. In this case, the functions of thermal conduction and movable bearing are integrated with each other in the heat coupling element. The heat pipe itself is arranged immovably in the shaft.

According to a further embodiment of the invention, the heat source is arranged in a distal end area of the shaft, in a middle portion of the shaft or in a proximal end area of the shaft.

The principle of the heat removal management according to the invention is effective regardless of where the one or more heat sources are located. On account of the principle of the "flexible heat sink" according to the invention, there is no preferential direction for the heat removal. Instead, the heat removal can take place from the distal end to the proximal end, from the proximal end to the distal end, or from a middle area of the shaft to the distal and/or proximal end, depending on where the coldest point of the heat pipe or of the shaft is located.

Correspondingly, according to another embodiment, the heat pipe is thermally coupled to the heat source via the distal heat pipe end, via a central portion between the distal heat pipe end and the proximal heat pipe end, or via the proximal heat pipe end.

On account of the principle of heat removal according to the invention, the working medium in the heat pipe seeks the currently or temporarily coldest point of the heat pipe as heat sink and the temporarily warmest point on the heat pipe as heat source ("flexible heat sink"). Therefore, within the context of the invention, it is not in fact necessary for the heat pipe to be connected at one end to the heat source and at the other end to the heat sink.

As has already been mentioned, it is possible, within the context of the invention, that the heat pipe can be thermally coupled not just to one heat source but also to a plurality of heat sources, wherein these heat sources are spaced apart from one another in the longitudinal direction of the shaft.

It is likewise possible for not just one heat pipe to be coupled thermally conductively to the one or more heat sources, but instead for several heat pipes to be arranged in the interior of the shaft and to be coupled thermally conductively to the one or more heat sources.

The several heat pipes can extend alongside each other in the shaft, or they can extend behind one another in the longitudinal direction, as has already been mentioned above.

According to another preferred embodiment, the heat pipe is a sintered heat pipe.

In a sintered heat pipe, which is made of copper for example, sintered copper particles are present on the inner face of the tube of the heat pipe. Sintered heat pipes are less gravitation-dependent than other types of heat pipes, i.e. their efficacy does not critically depend on whether they extend parallel or transverse to the force of gravity.

Within the context of the invention, it is moreover advantageous if several thin heat pipes are used instead of one heat pipe of large diameter. In addition to being less position-dependent, thin heat pipes have the advantage of a greater surface to volume ratio than a heat pipe with a large diameter.

Further advantages and features will become clear from the following description and from the attached drawing.

It will be appreciated that the aforementioned features and the features still to be explained below can be used not only in the cited combination but also in other combinations or singly, without departing from the scope of the present invention.

BRIEF DESCRIPTION OF THE DRAWINGS

Illustrative embodiments of the invention are shown in the drawings and are described in more detail below with reference to said drawings, in which.

DESCRIPTION OF EXEMPLARY PREFERRED EMBODIMENTS

Figure 1:
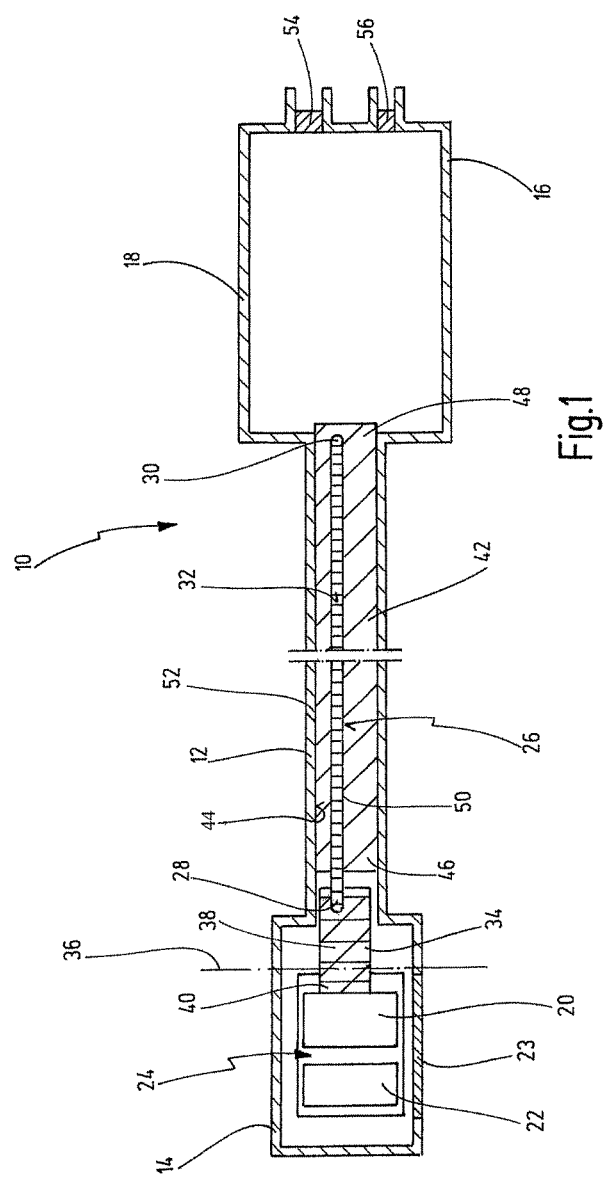
FIG. 1 shows a schematic diagram of an optical medical instrument in longitudinal section according to an illustrative embodiment.

FIG. 1 shows an optical medical instrument 10 in a schematic view. The instrument 10 is an endoscope or an exoscope.

Generally, the instrument 10 has an elongate tubular shaft 12 between a distal end 14 and a proximal end 16. The shaft 12 is depicted in an interrupted view in order to show that the shaft 12 can extend over a great length. In FIG. 1, the distal end area of the instrument 10 and the proximal end area of the instrument 10 are also shown as being wider, although this is to be understood only by way of example. The proximal end 16 is designed here as an instrument head housing 18. The shaft 12 and the instrument head housing 18 constitute the housing for the components located therein. The instrument head housing 18 can belong to the shaft 12. Likewise, the shaft 12 itself is to be understood as a housing. The housing can be hermetically sealed.

The components in the shaft 12 include electronic elements arranged in the distal end area of the shaft 12, such as one or more image sensors, populated printed circuit boards or the like, which are designated jointly in FIG. 1 by reference sign 20 and are referred to hereinbelow as the electronics unit 20.

Further components in the distal end area serve for illumination and are designated jointly by reference sign 22 and are referred to hereinbelow as the illumination unit 22. The illumination unit 22 can be formed by one or more light sources such as LEDs or by the light-emitting ends of optical fibres.

A window 23, which extends parallel to the longitudinal direction of the shaft 12 in the illustrative embodiment shown, serves as the light output for the illumination unit 22 and as the light input for the one or more image sensors of the electronics unit 20. While the viewing direction of the instrument 10 in the illustrative embodiment shown is thus 90° to the longitudinal direction of the shaft 12, it goes without saying that other viewing directions such as 0°, 30°, 60° and the like are also possible, as are customary in particular in endoscopes.

The electronics unit 20 and if appropriate the illumination unit 22 represent a heat source 24 that generates lost heat. The electronics unit 20 in particular generates a large amount of lost heat, which has to be removed from the electronics unit 20, since it is known that the performance of electronic elements falls as the temperature increases.

In order to efficiently remove the lost heat from the heat source 24, the instrument 10 has a heat removal management system, which is described below.

The latter includes a heat pipe 26 which extends inside the shaft 12 in an elongate area between the distal end 14 and the proximal end 16 and which has a distal heat pipe end 28 and a proximal heat pipe end 30.

The heat pipe 26 is a heating tube which encloses a hermetically encapsulated volume filled with a working medium, for example water or ammonia, that fills the volume to a small extent in the liquid state and to a greater extent in the vapour state. The working medium begins to evaporate when heat enters the heat pipe 26, wherein the resulting vapour flows away from the site of introduction of the heat. On its outer surface, the heat pipe 26 is not thermally insulated anywhere along the entire length of the heat pipe 26.

All customary forms of heat pipes can be used as the heat pipe 26, although in the present case the heat pipe 26 is preferably designed as a sintered heat pipe. In contrast to other types of heat pipes, the function of sintered heat pipes is less dependent on position with respect to gravitation. Furthermore, the heat pipe 26 should not be too large in cross section and instead should be somewhat narrow, since this likewise further reduces the positional dependency of the heat pipe 26 with respect to gravitation and, in addition, the surface to volume ratio is greater and therefore more favourable than in the case of a thicker heat pipe. A greater surface to volume ratio helps improve the heat transfer from the heat pipe 26 to its environment. The heat pipe 26 can have a round cross section, although it can also have an oval or flattened cross section.

The heat pipe 26 is thermally coupled, here thermally conductively coupled, to the heat source 24 in order to collect heat from the heat source 24 and remove the heat from the heat source 24.

For this purpose, the heat pipe 26, in the present illustrative embodiment the heat pipe 28, is connected thermally conductively to the heat source 24 via a heat coupling element 34.

The heat coupling element 34 can be in the form of a heat conduction plate or heat conduction body made of a material with good thermal conductivity, for example copper or aluminum. The connection of the heat source 24 to the heat coupling element 34 can be improved by the introduction of a graphite foil (not shown).

In the case where the instrument 10 is, for example, a video exoscope or a video endoscope with a pivotable camera (image sensor or image sensors of the electronics unit 20), wherein the camera is pivotable about a pivot axis 36 for example, the heat coupling element 34 is designed as a thermally conductive bearing with a degree of freedom of movement in rotation about the pivot axis 36. In this case, the heat coupling element 34 can be composed of a stationary part 38, and of a part 40 that is movable (rotatable) relative to the latter, wherein the movable part 40 is connected to the heat source 24. It will be appreciated that the connection between the stationary part 38 and the part 40, movable relative thereto, of the heat coupling element 34 has to provide good thermal conductivity. This can be provided or improved by a heat-conducting intermediate material between the bearing halves (parts 38 and 40), for example graphite foil. It will be appreciated that the pivot axis of the camera can also coincide with the viewing axis of the instrument 10.

The heat pipe 26 is connected to the heat coupling element 34 in particular with a form fit, which can be achieved by the fact that, in the present case, the distal heat pipe end 28 is pressed into a recess of the heat coupling element 34. The connection of the heat pipe 26 to the heat coupling element 34 can be supported by a thermally conductive adhesive, wherein this additional cohesive bond fixes the degrees of freedom that are still open despite the form fit.

The lost heat generated by the heat source 24 (electronics unit 20, illumination unit 22) is transferred via the heat coupling element 34 to the heat pipe 26, in this case to the distal heat pipe end 28. In the heat removal management system according to the invention, provision is now made that this lost heat is not necessarily always conveyed from the heat pipe 26 to the proximal heat pipe end 30 and released there, and instead the heat removal management system according to the invention is based on a "flexible heat sink", as is explained below.

The principle of the "flexible heat sink" is that the heat pipe 26, between the distal heat pipe end 28 and the proximal heat pipe end 30, is connected thermally conductively and two-dimensionally to the shaft 12 over at least a partial length of the heat pipe 26 and over at least a partial circumference of the heat pipe 26 (circumference is to be understood as the circumference with respect to the longitudinal direction of the heat pipe 26), such that heat from the heat pipe 26 is removed, over at least a partial length and at least a partial circumference of the shaft 12 serving as the heat sink, to the environment. In the illustrative embodiment shown in FIG. 1, the heat pipe 26 is thermally conductively coupled to the shaft 12 over almost or completely the total length of the heat pipe 26. The heat pipe 26 extends here over more than half the length of the shaft 12 and is coupled thermally conductively to the shaft 12 over more than half the length of the latter.

In the illustrative embodiment in FIG. 1, the heat pipe 26 is thermally conductively coupled to the shaft 12 about the entire circumference via a heat sink body 42. However, a connection about part of the circumference is likewise possible. On the one hand, the heat sink body 42 is in form-fit contact with the heat pipe 26 and, on the other hand, the heat sink body 42 is in form-fit contact with the inner face 44 or inner wall of the shaft 12.

While the heat pipe 26 in the illustrative embodiment in FIG. 1 is coupled thermally conductively to the shaft 12 via the heat sink body 42, it is possible, in other illustrative embodiments described below, that the heat pipe 26, about at least part of its circumference, is in direct form-fit contact with the inner face 44 and, about another part of the circumference, is thermally conductively coupled to the shaft 12 via a heat sink body.

The principle of the "flexible heat sink" according to the invention means that the current heat sink is always located at the site of the lowest current temperature on the surface of the heat pipe 26. The function of the heat pipe 26 is not limited to the heat sink having to be located at one of the two heat pipe ends, here at the proximal heat pipe end 30. Instead, the working medium in the heat pipe 26 seeks the currently coldest point of the heat pipe 26 as heat sink and the temporarily warmest point on the heat pipe 26 as heat source. However, in the present case, the location of the heat source 24 is always fixed. The heat sink, i.e. the coldest place along the shaft 12, is not fixed. By means of the heat pipe 26 being connected to the shaft 12 as uniformly as possible and along optimally the full length, the heat sink can be located anywhere along the heat pipe 26. The position of the heat sink along the shaft 12 is therefore flexible, depending on the function of the heat pipe 26. This has the effect that the heat is distributed uniformly across the existing surface of the shaft 12 and the temperature difference is thus kept as low as possible.

In the illustrative embodiment in FIG. 1, the heat sink body 42 is designed in particular in one piece and extends almost the entire length of the heat pipe 26 between a distal end 46 and a proximal end 48 of the heat sink body 42. It will be appreciated that the heat sink body 42 has one or more longitudinally continuous openings (not shown) or lateral longitudinal cuttings that are suitable for the routing of electricity supply lines and data transmission lines and, if appropriate, for the routing of optical fibers.

The form-fit connection of the heat pipe 26 to the heat sink body 42, which connection is designated by reference sign 50, and the form-fit connection of the heat sink body 42 to the inner face 44 of the shaft 12, as indicated by 52, can be fixed by cohesive joining, such as gluing, or with solder, wherein the joining material must have good thermal conductivity. However, if a different lengthwise extent between heat pipe 26, heat sink body 42 and/or shaft 12 has to be taken into consideration, an additional cohesive connection of this kind is completely or partially dispensed with.

At the proximal shaft end 16 in FIG. 1, there is also an attachment 54 for the voltage supply and data transfer for the electronics 20, and an attachment 56 for the lighting, for example for attaching a fiber optic cable.

Further illustrative embodiments are described below with reference to FIGS. 2 to 13. Elements in FIGS. 2 to 13 that are identical or similar to elements in FIG. 1 are provided with the same reference signs, if appropriate with the addition of letters.

Only the respective differences from the illustrative embodiment in FIG. 1 are described below.

Figure 2:
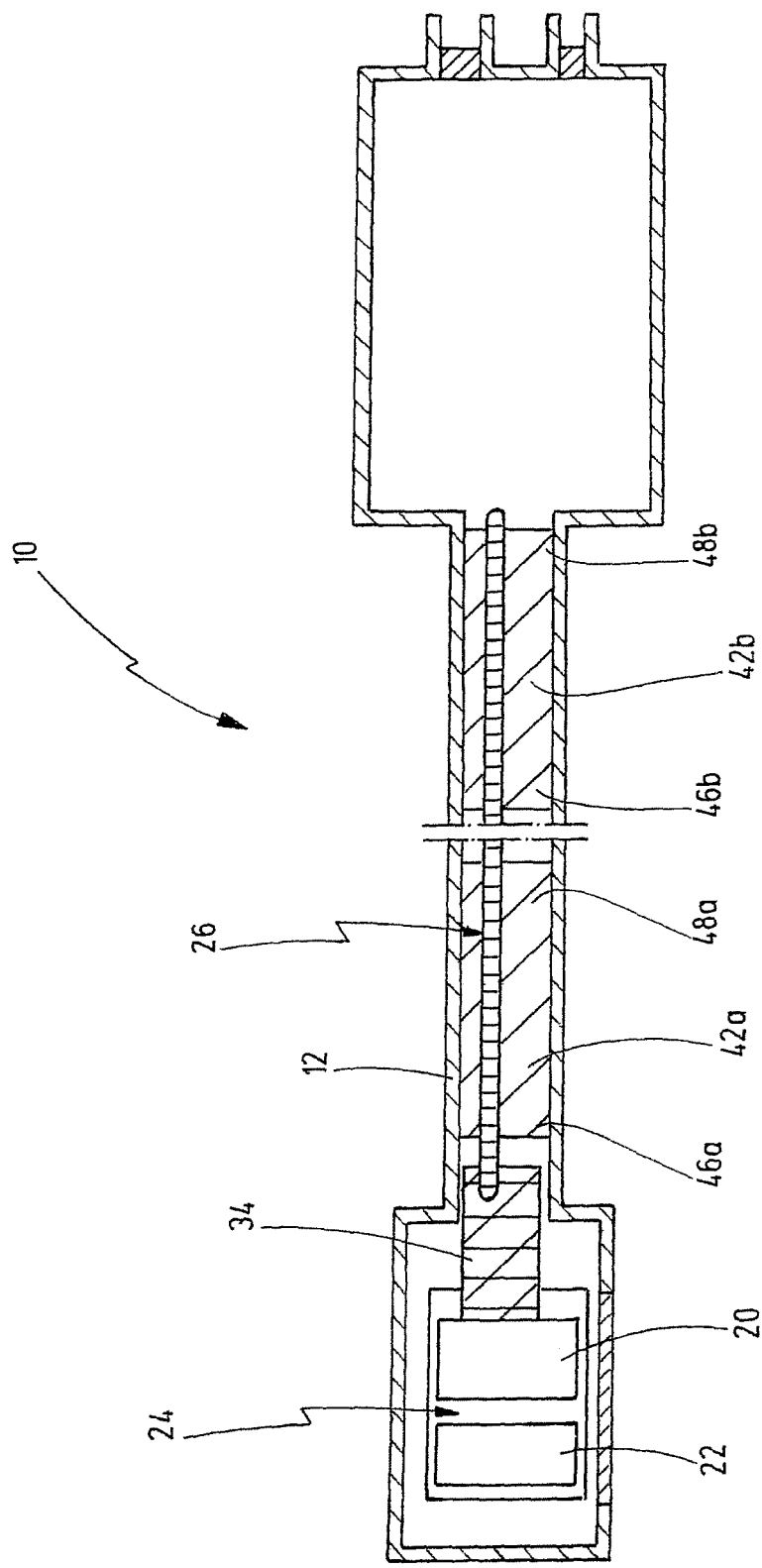
FIG. 2 shows a schematic diagram of an optical medical instrument in longitudinal section according to a further illustrative embodiment.

In the instrument in FIG. 2, the heat pipe 26 is coupled thermally conductively to the shaft 12 via a plurality of heat sink bodies, here via two heat sink bodies 42a and 42b, wherein the heat sink bodies 42a and 42b are distributed along the heat pipe 26 and are arranged spaced apart from each other. The heat sink body 42a has a distal end 46a and a proximal end 48a, and the heat sink body 42b has a distal end 46b and a proximal end 48b.

Figure 3:
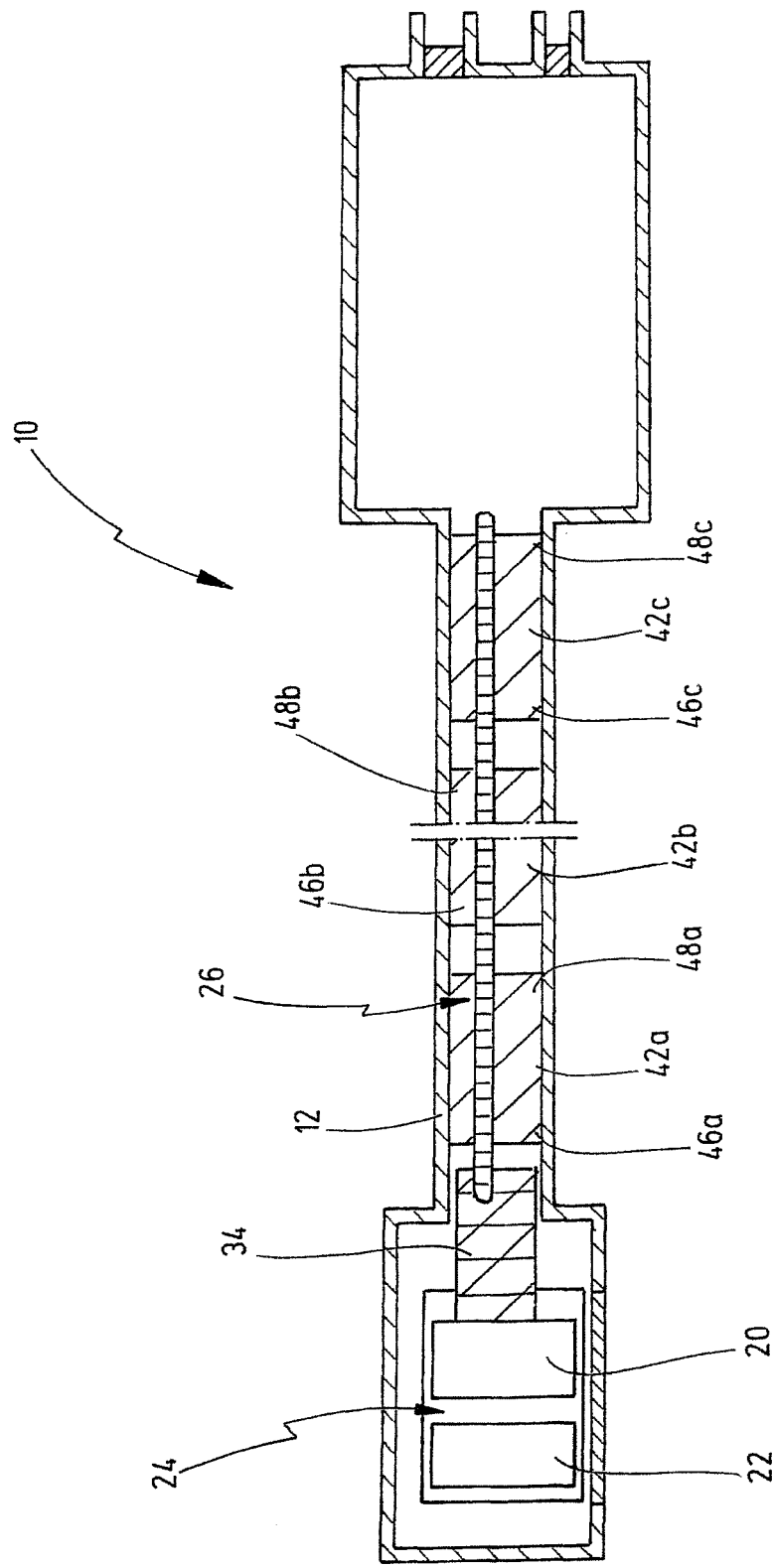
FIG. 3 shows a schematic diagram of an optical medical instrument in longitudinal section according to a further illustrative embodiment.

The instrument 10 according to FIG. 3 likewise has a plurality of heat sink bodies, here three heat sink bodies 42a, 42b and 42c, which are distributed along the heat pipe 26 and are arranged spaced apart from one another and couple the heat pipe 26 thermally conductively to the shaft 12. The heat sink body 42a has a distal end 46a and a proximal end 48a, the heat sink body 42b has a distal end 46b and a proximal end 48b, and the heat sink body 42c has a distal end 46c and a proximal end 48c.

Figure 4:
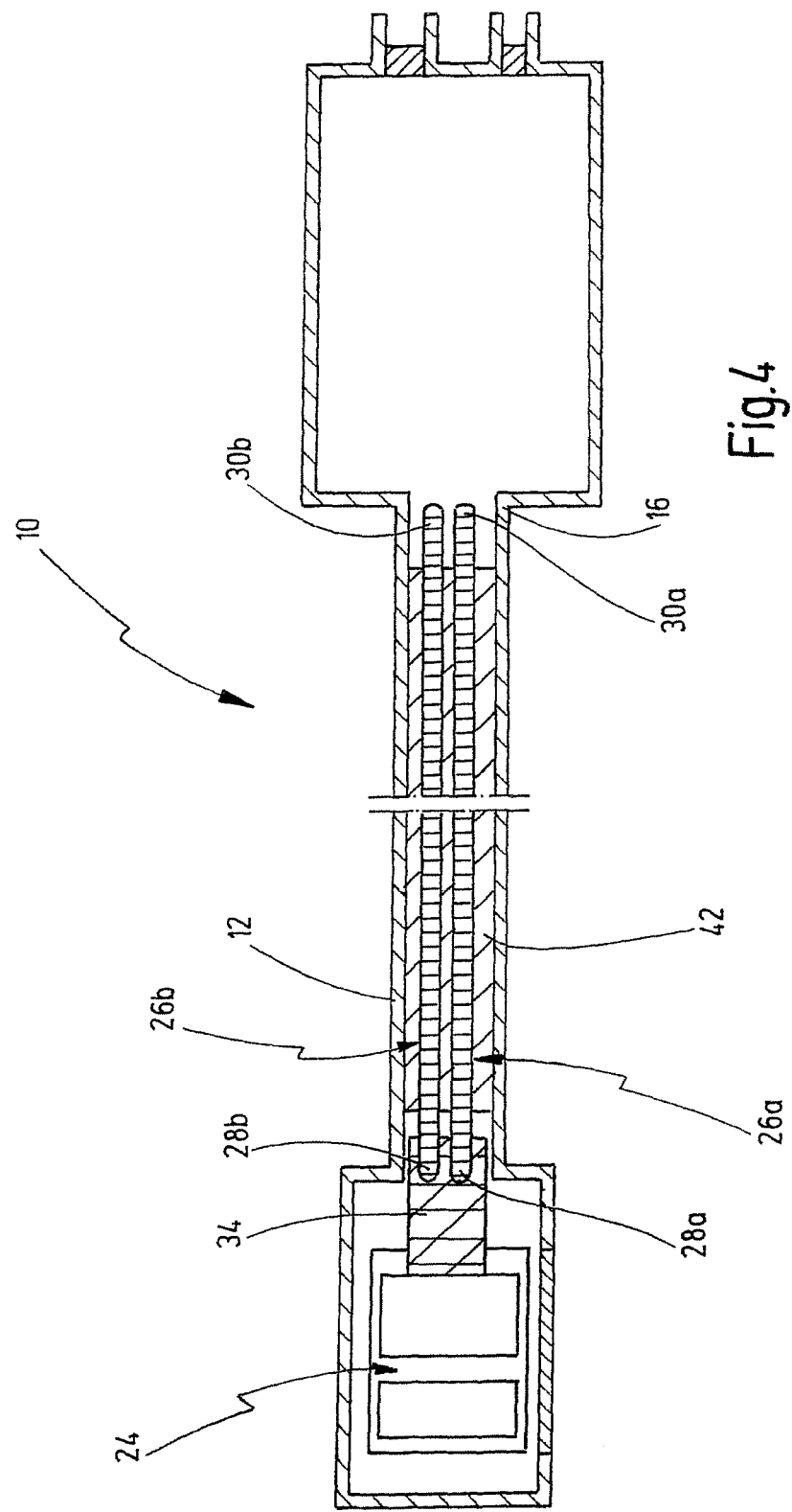
FIG. 4 shows a schematic diagram of an optical medical instrument in longitudinal section according to a further illustrative embodiment.

In contrast to the previous illustrative embodiments, the instrument 10 in FIG. 4 has two heat pipes 26a and 26b which are both, on the one hand, connected thermally conductively to the heat source 24 via the heat coupling element 34 and, on the other hand, are connected thermally conductively to the shaft 12, the latter connection being effected via the heat sink body 42, which is here once again designed in one piece.

Viewed transversely with respect to the longitudinal direction of the shaft 12, the two heat pipes 26a and 26b are arranged next to each other and both extend from the heat coupling element 34 as far as the area of the proximal end 16 of the shaft. The heat pipe 26a has a distal heat pipe end 28a and a proximal heat pipe end 30a, and the heat pipe 26b has a distal heat pipe end 28b and a proximal heat pipe end 30b.

As has already been mentioned above, the use of several thin heat pipes is preferred to the use of just one heat pipe with a larger cross section, by virtue of the reduced positional dependency of the heat pipes with respect to gravitation and the increased surface to volume ratio.

Figure 5:
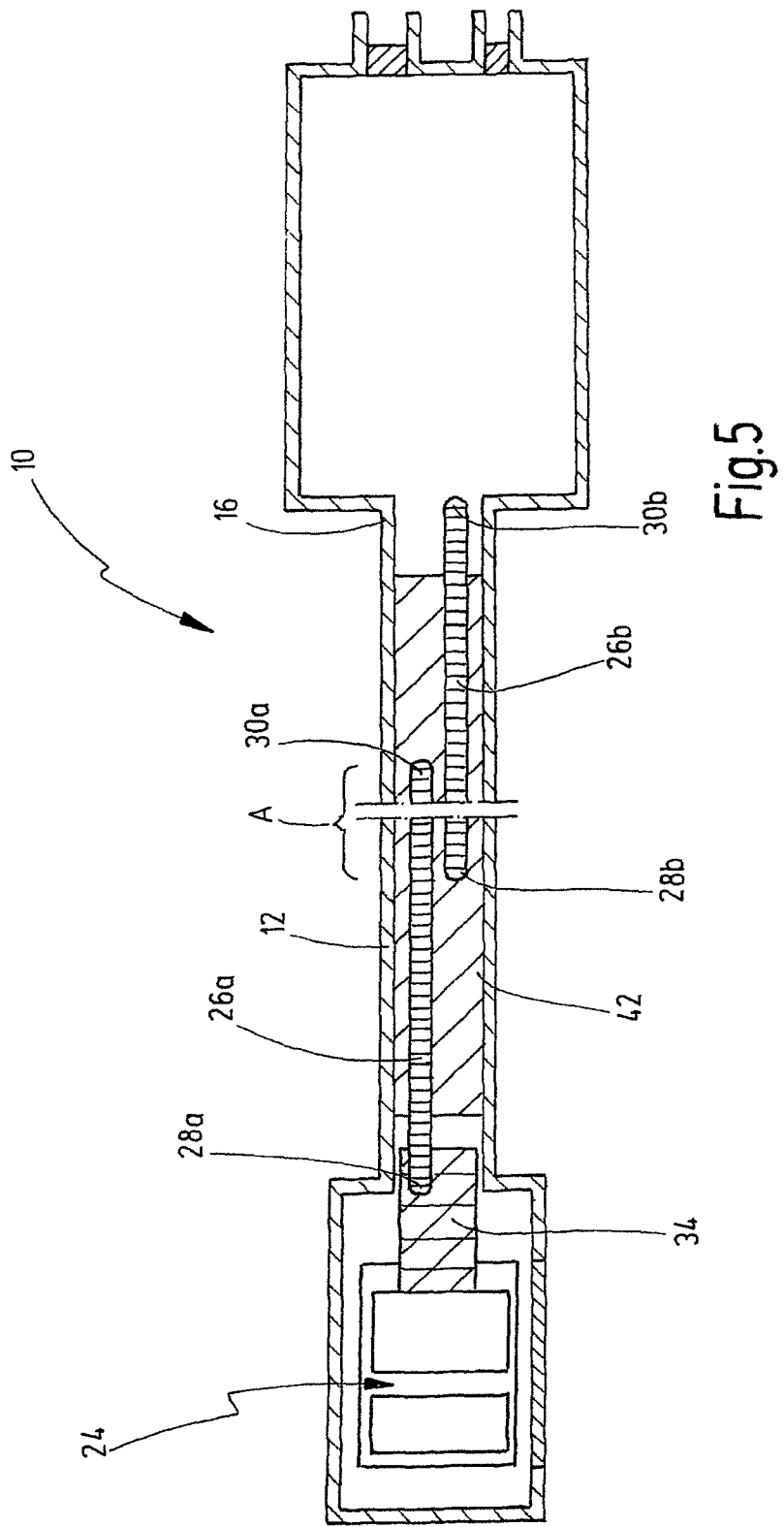
FIG. 5 shows a schematic diagram of an optical medical instrument in longitudinal section according to a further illustrative embodiment.

The instrument 10 in the illustrative embodiment in FIG. 5 likewise has two heat pipes 26a and 26b, but in this illustrative embodiment only the heat pipe 26a is coupled thermally conductively to the heat coupling element 34. The heat pipe 26a has a distal heat pipe end 28a and a proximal heat pipe end 30a.

The second heat pipe 26b has a distal heat pipe end 28b and a proximal heat pipe end 30b. Both heat pipes 26a and 26b extend only over a shorter part of the length of the shaft 12 compared to the previous illustrative embodiments, although the two heat pipes 26a and 26b together extend over the same area as in the previous illustrative embodiments. The two heat pipes 26a and 26b have an overlap area A providing a thermally conductive coupling to each other, such that a heat transfer can take place between the two heat pipes 26a and 26b in this area A.

Figure 6:
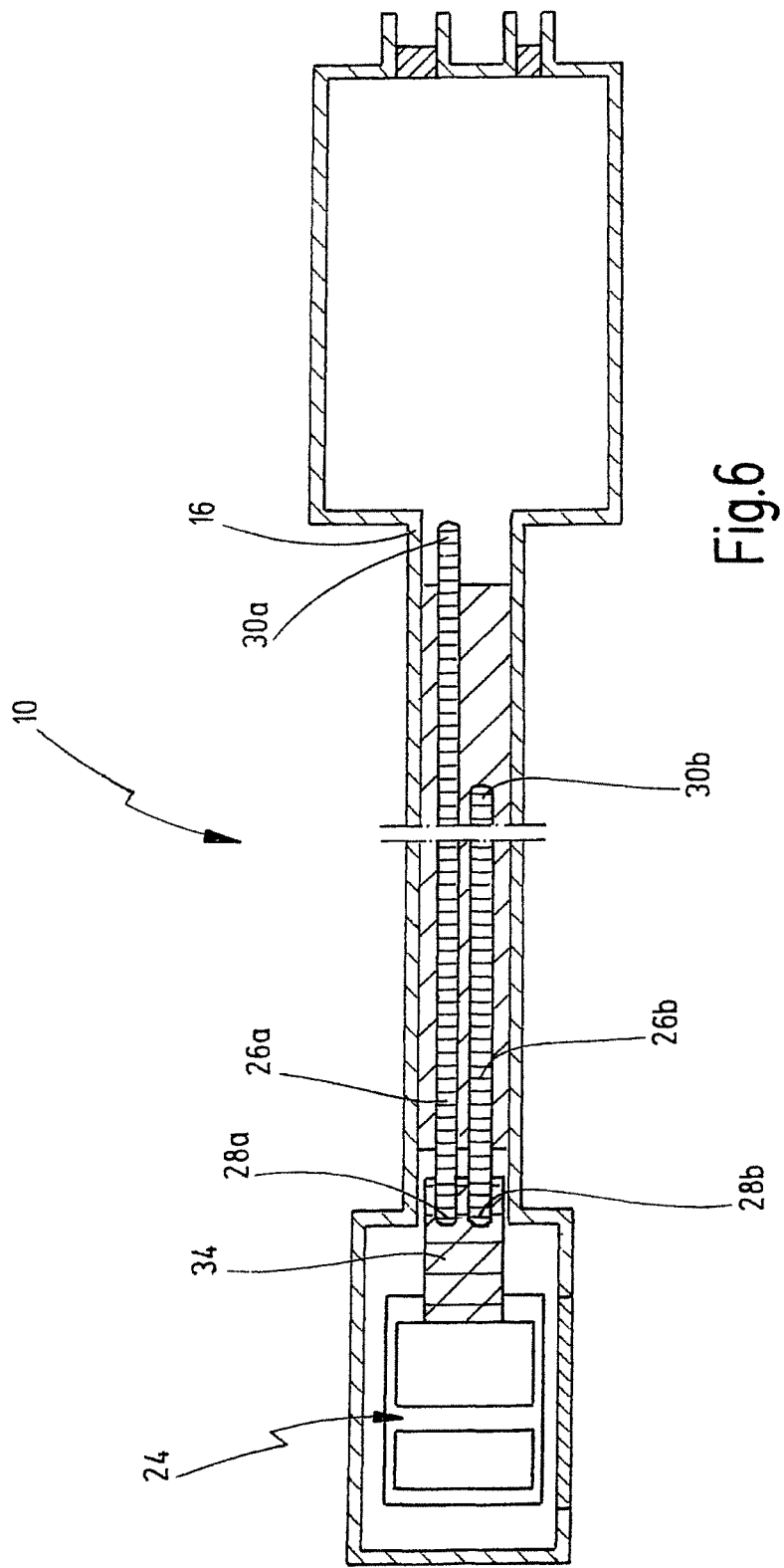
FIG. 6 shows a schematic diagram of an optical medical instrument in longitudinal section according to a further illustrative embodiment.

The instrument 10 in FIG. 6 likewise has two heat pipes 26a and 26b, wherein both heat pipes 26a and 26b are coupled thermally conductively to the heat source 24 via the heat coupling element 34. While the heat pipe 26a extends from the heat coupling element 34 as far as the proximal end area of the shaft 12, the heat pipe 26b is shorter and ends with its proximal heat pipe end 30b at a distance from the proximal heat pipe end 30a.

Figure 7:
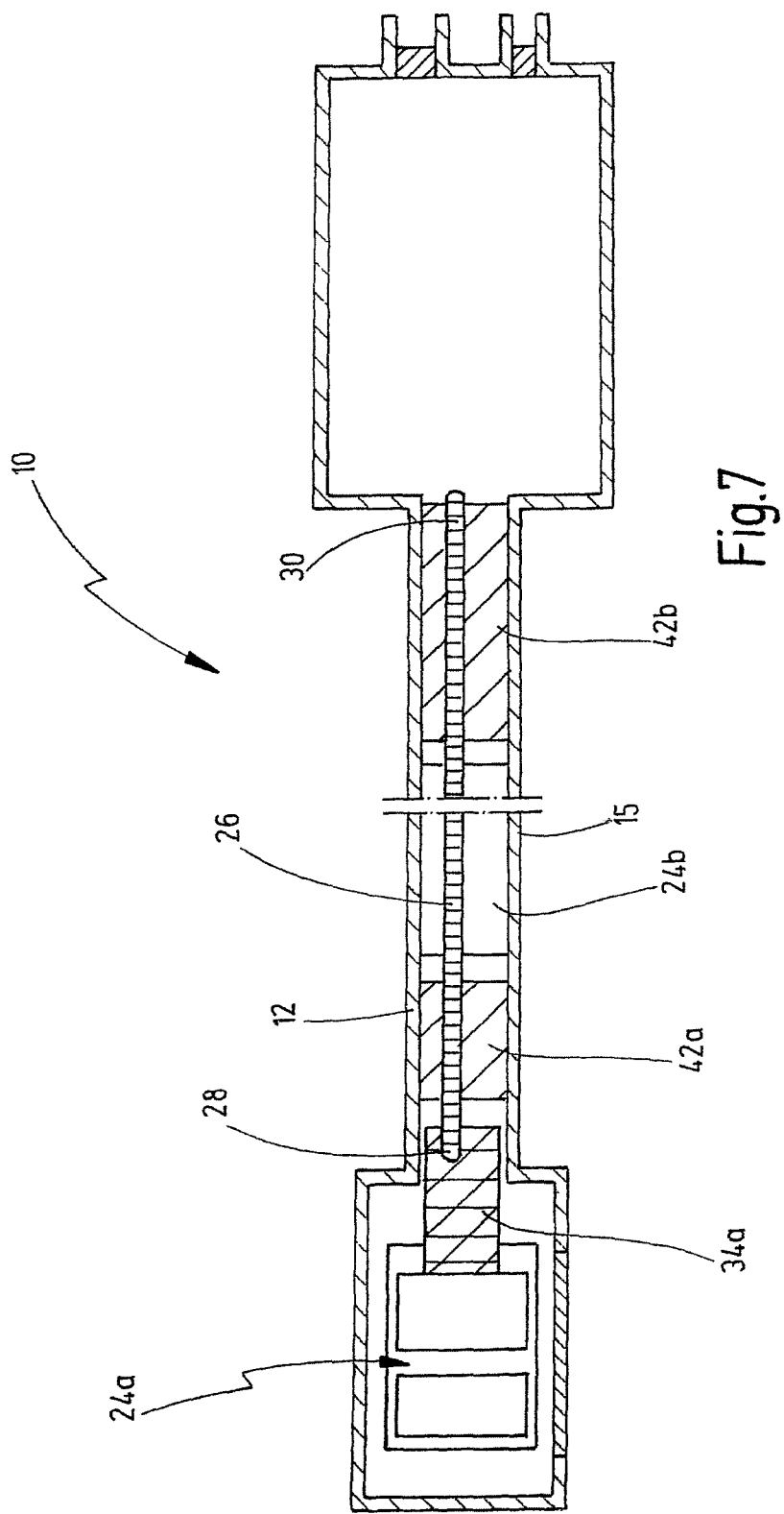
FIG. 7 shows a schematic diagram of an optical medical instrument in longitudinal section according to a further illustrative embodiment.

Whereas in the previous illustrative embodiments there is only one heat source, specifically the heat source 24 in the distal end area of the shaft 12, the instrument 10 in FIG. 7 has two heat sources, specifically a first heat source 24a, which corresponds to the heat source 24 in the previous illustrative embodiments, and a second heat source 24b, which is located in a middle portion 15 of the shaft 12 between the distal end 14 and the proximal end 16 of the shaft. The additional heat source 24b can be caused, for example, by further electronic components in the central portion 15 of the shaft 12. The heat pipe 26 is thermally coupled to this additional heat source 24b in order to collect heat from the heat source 24b and remove the heat to a colder point along the shaft 12. The principle of the "flexible heat sink" applies here too. Depending on where the currently coldest point of the shaft 12 is located, the heat collected from the heat source 24b is conveyed in the distal or proximal direction and is removed to the environment at the currently coldest location.

In the illustrative embodiment in FIG. 7, the heat pipe 26 is coupled thermally conductively to the shaft 12 via two heat sink bodies 42a and 42b.

Figure 8:
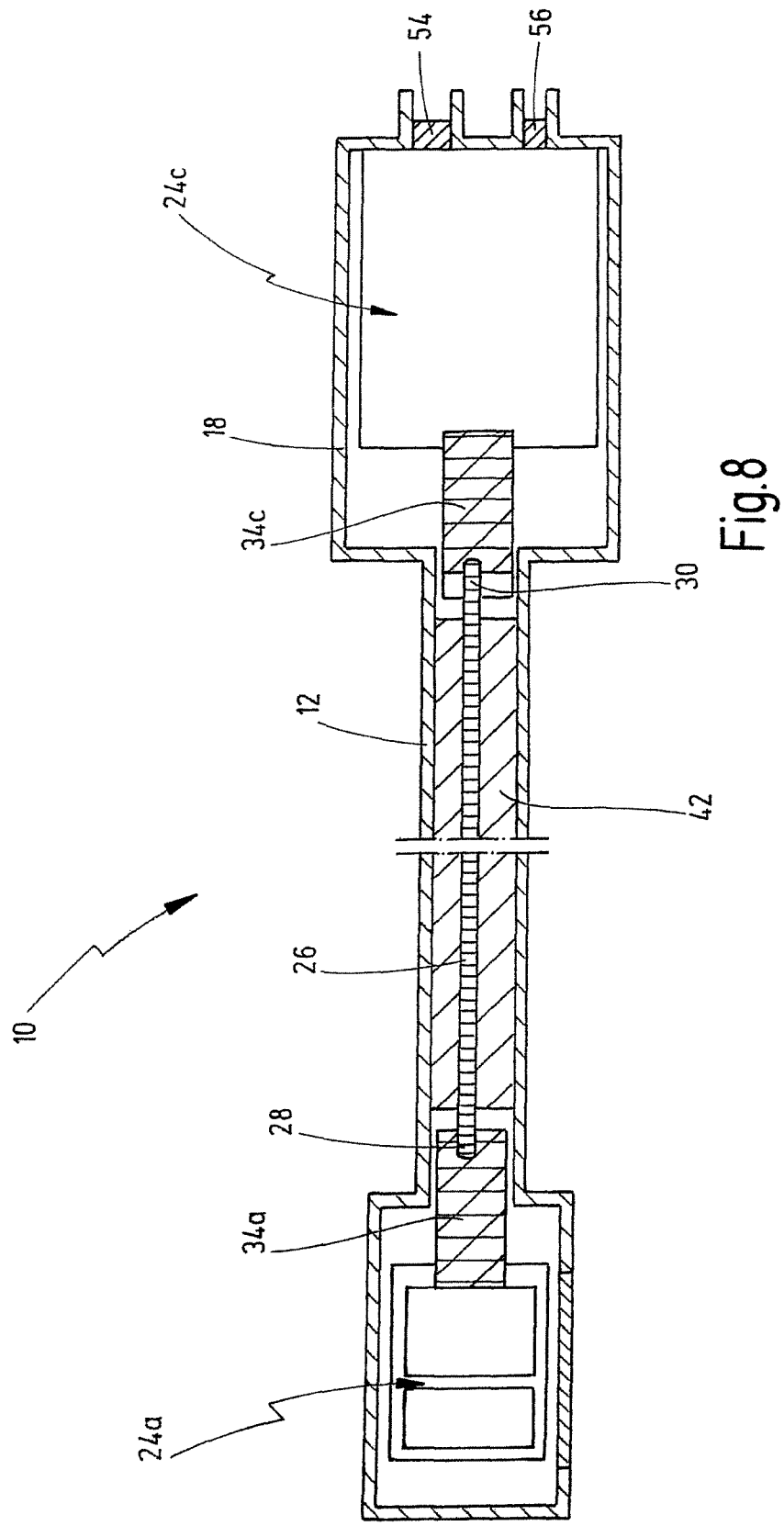
FIG. 8 shows a schematic diagram of an optical medical instrument in longitudinal section according to a further illustrative embodiment.

The instrument 10 in FIG. 8 likewise has two heat sources 24a and 24c. The heat source 24a is located in the distal end area of the shaft 12, and the heat source 24c is located in the proximal end area 16 of the shaft or in the instrument head housing 18. This proximal heat source 24c can be caused by electronic components present in the instrument head housing 18, for the power electronics or data processing, or by the attachments and couplings 54 and 56. The heat pipe 26 is coupled thermally conductively to the additional heat source 24c via a heat sink element 34c and is connected to the distal heat source 24a via a heat coupling element 34a. The heat coupling elements 34a and 34c can be designed like the heat coupling element 34 according to the above description, and the heat coupling element 34c does not have to be designed as a movable bearing.

The principle of the "flexible heat sink" applies also in the illustrative embodiment in FIG. 8, wherein the heat collected from the heat source 24a is removed by the heat pipe 26 in the proximal direction to a currently coldest point of the shaft 12, and the heat collected from the heat source 24c is removed in the distal direction to a currently coldest point of the shaft 12.

Figure 9:
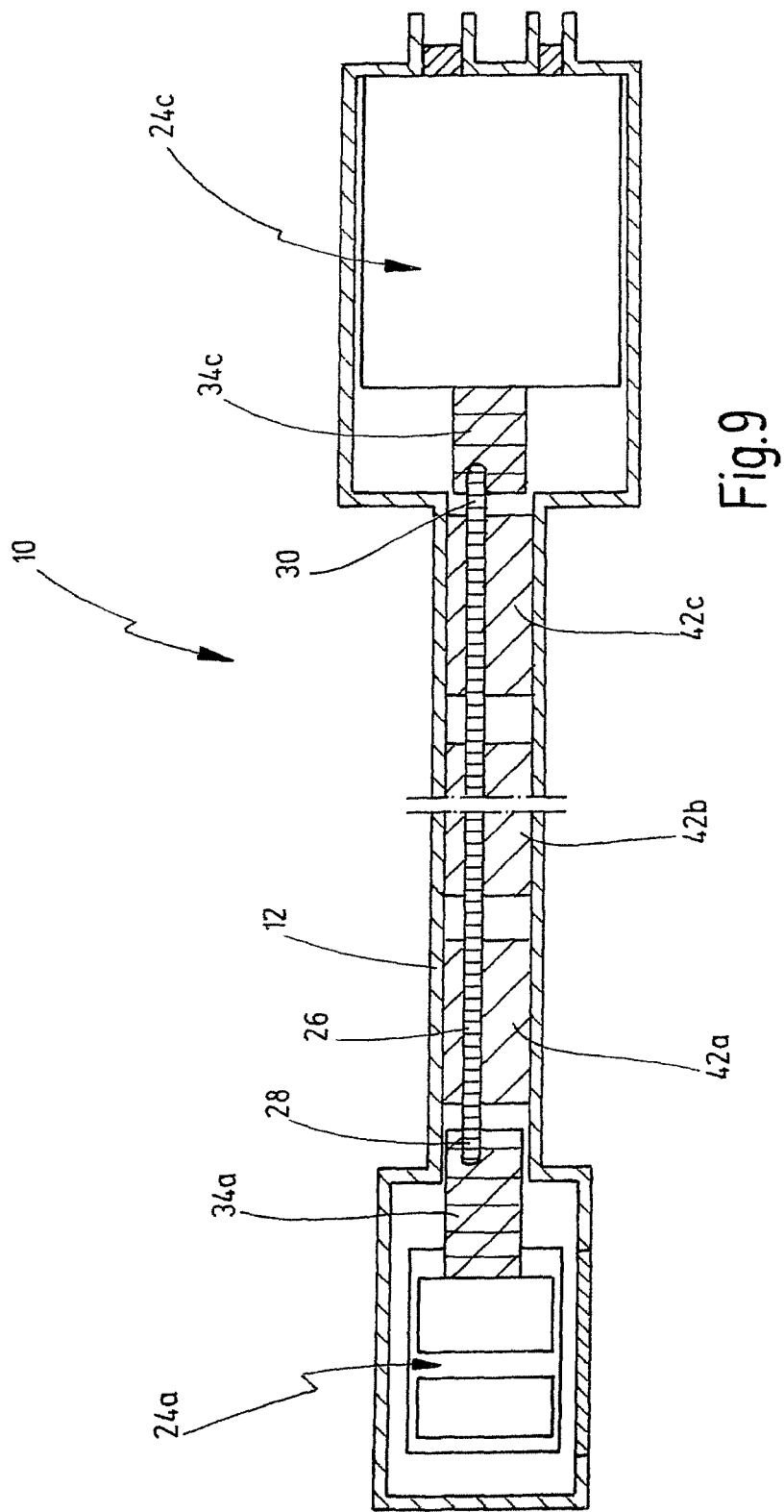
FIG. 9 shows a schematic diagram of an optical medical instrument in longitudinal section according to a further illustrative embodiment.

The illustrative embodiment according to FIG. 9 corresponds to the illustrative embodiment in FIG. 8 except that, instead of the one-piece heat sink body 42 in FIG. 8, a plurality of heat sink bodies 42a, 42b, 42c are present as in the illustrative embodiment in FIG. 3.

Figure 10:
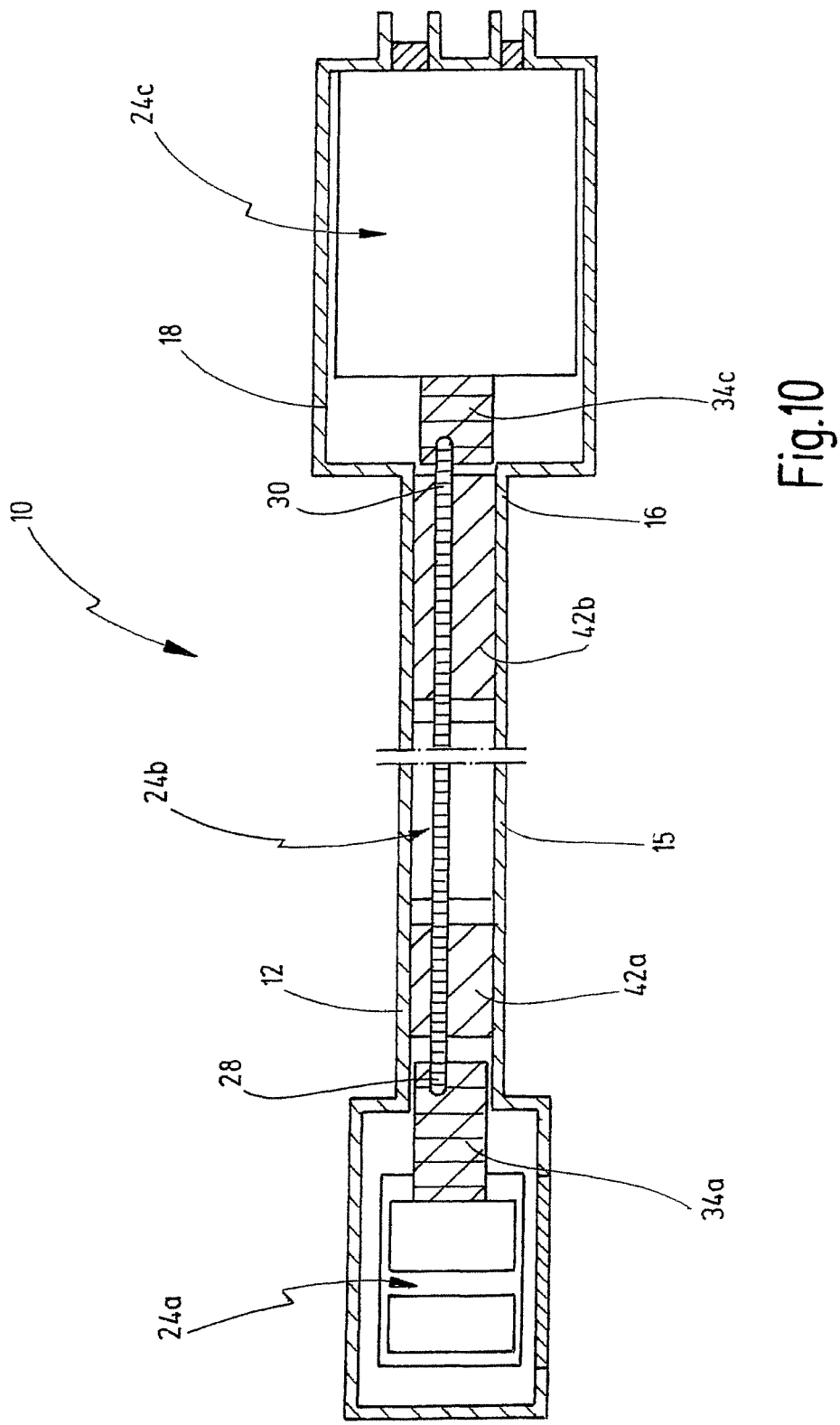
FIG. 10 shows a schematic diagram of an optical medical instrument in longitudinal section according to a further illustrative embodiment.

FIG. 10 shows an illustrative embodiment of the instrument 10 in which three heat sources 24a, 24b and 24c are present in total, corresponding to a combination of the illustrative embodiments in FIGS. 7 and 9. The heat source 24a is located in the distal end area of the shaft 12, the heat source 24b is located in the middle portion 15 of the shaft 12, and the heat source 24c is located in the proximal end area of the shaft 12 or in the instrument head 18. The principle of the "flexible heat sink" also applies in this illustrative embodiment.

Figure 11:
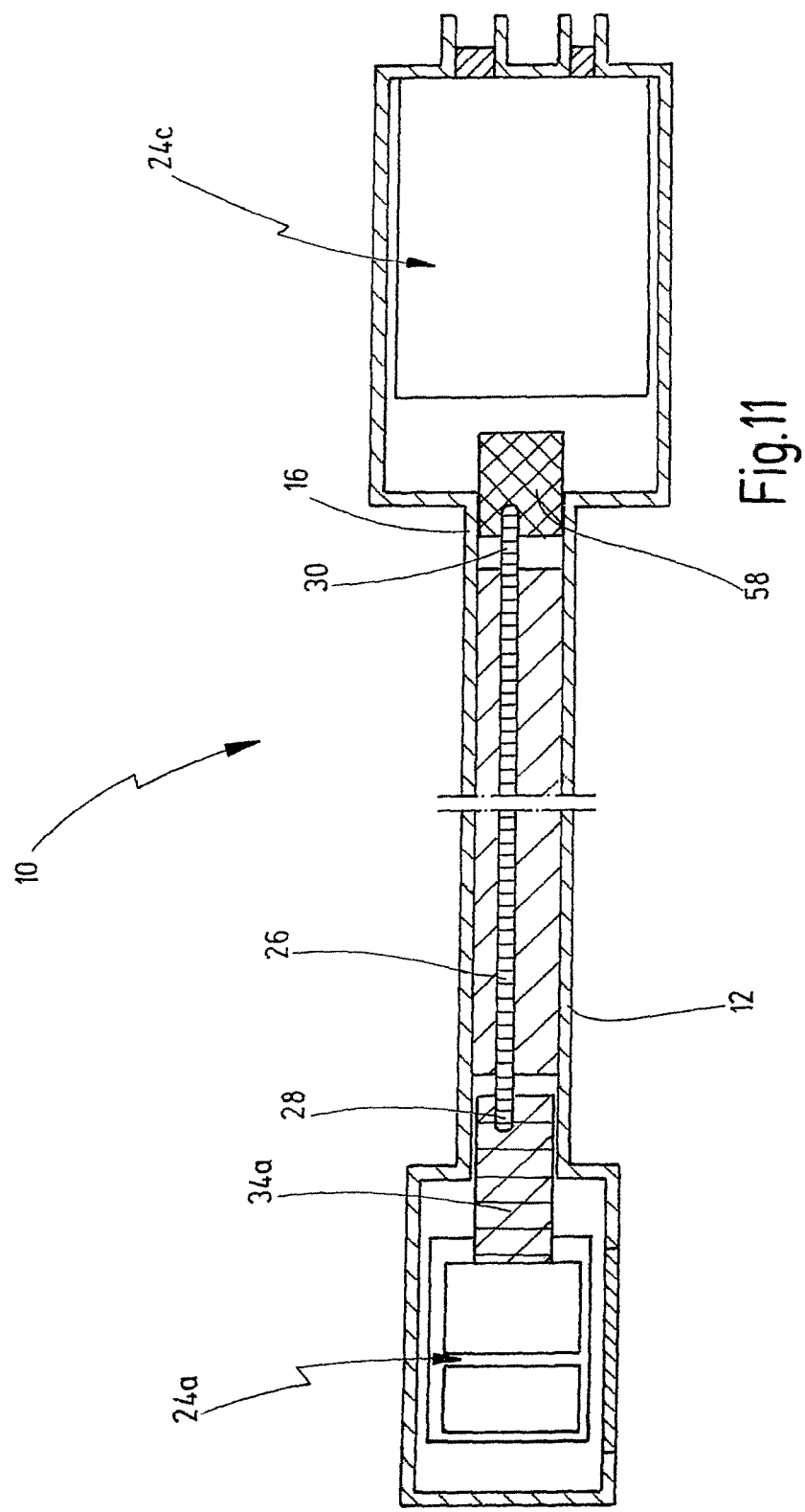
FIG. 11 shows a schematic diagram of an optical medical instrument according to a further illustrative embodiment.

The illustrative embodiment in FIG. 11 differs from the previous illustrative embodiments in that the heat pipe 26 in the proximal end area of the shaft 12 is thermally insulated from the shaft 12 by a thermal insulator 58. This configuration is provided for the case where, for example, the lost heat from the proximal heat source 24c is intended to be dissipated only in the proximal direction. This is the case, for example, when different temperatures are permissible on different surfaces along the instrument 10.

Figure 12:
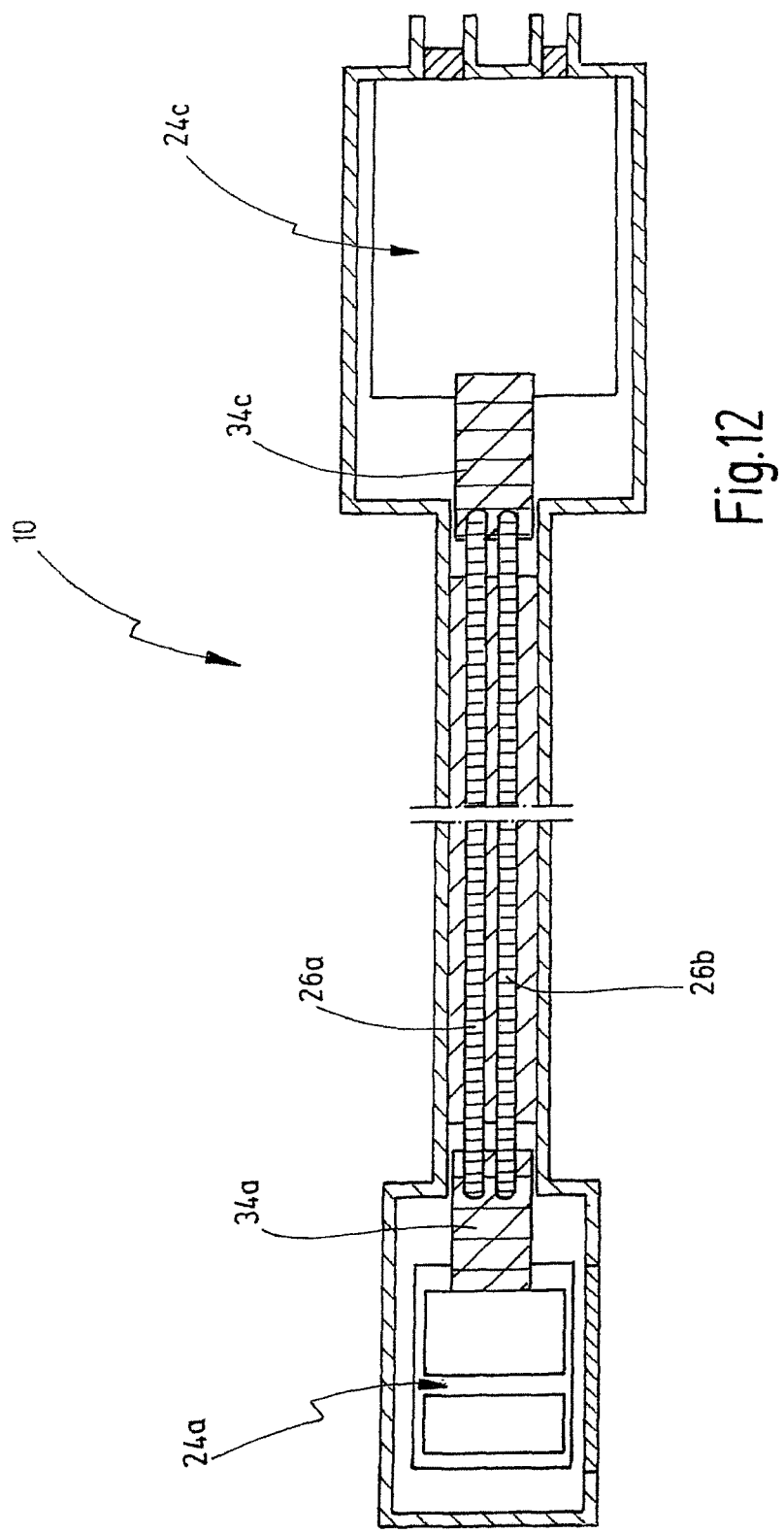
FIG. 12 shows a schematic diagram of an optical medical instrument in longitudinal section according to a further illustrative embodiment.

FIG. 12 shows an illustrative embodiment of the instrument 10 representing a combination of the illustrative embodiments in FIGS. 4 and 8, i.e. the instrument 10 in this illustrative embodiment has the two heat sources 24a and 24c and also the two heat pipes 26a and 26b, both of which are coupled thermally conductively both to the distal heat source 24a and also to the proximal heat source 24c.

Figure 13:
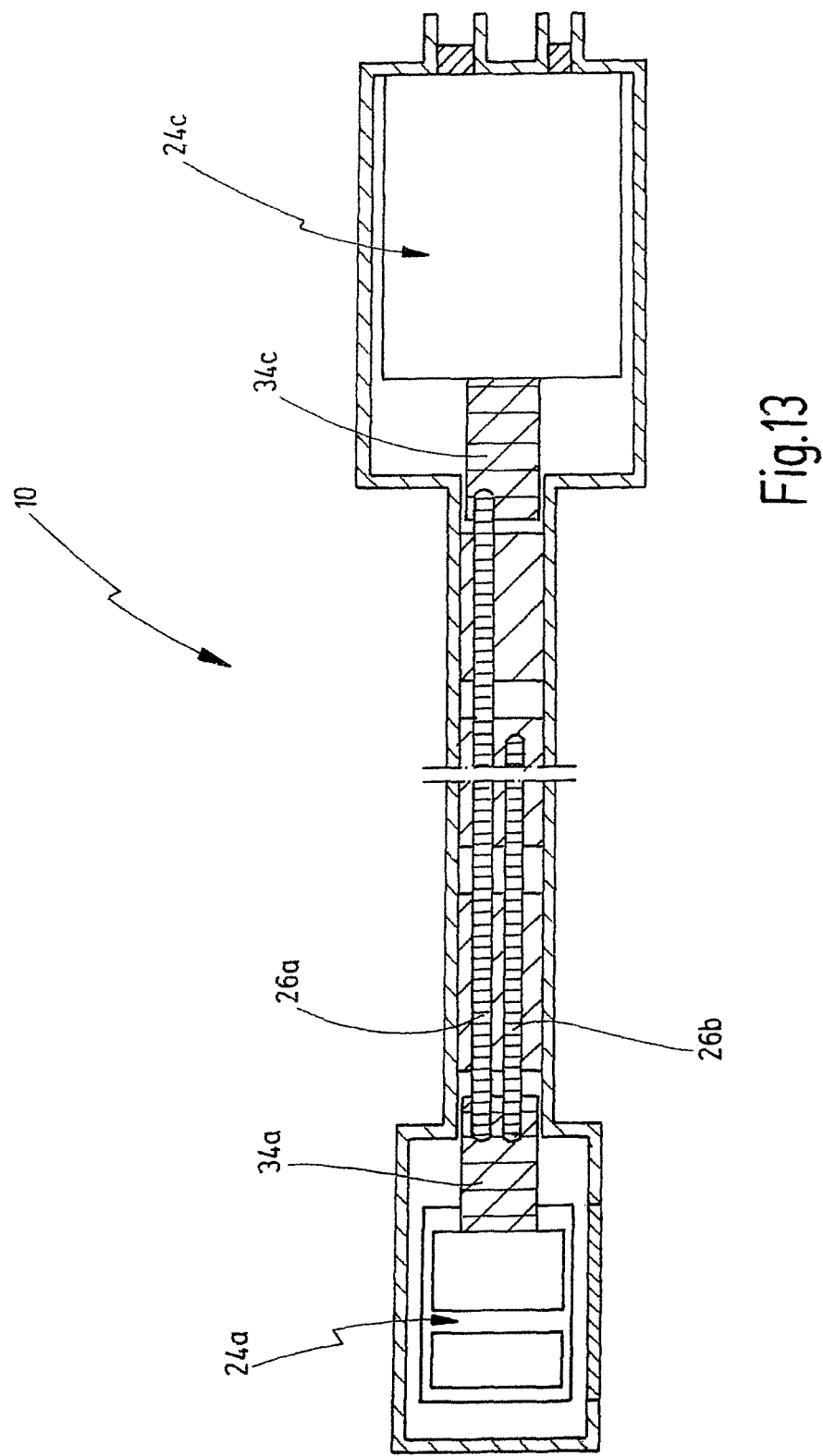
FIG. 13 shows a schematic diagram of an optical medical instrument in longitudinal section according to a further illustrative embodiment.

FIG. 13 shows the instrument 10 in an illustrative embodiment representing a combination of the illustrative embodiments in FIGS. 6 and 8. In this illustrative embodiment, the two heat pipes 26a and 26b are both coupled thermally conductively in common to the distal heat source 24a, whereas only the heat pipe 26a is coupled thermally conductively to the proximal heat source 24c. A configuration of this kind may be considered if the distal heat source 24a generates a greater amount of lost heat than the proximal heat source 24c. By connecting both heat pipes 26a and 26b to the heat source 24a, the greater amount of lost heat can be more effectively removed from the latter, whereas the one heat pipe 26a is sufficient for removing the lost heat from the heat source 24b.

Further illustrative embodiments are described with reference to FIGS. 14 to 17.

Figure 14:
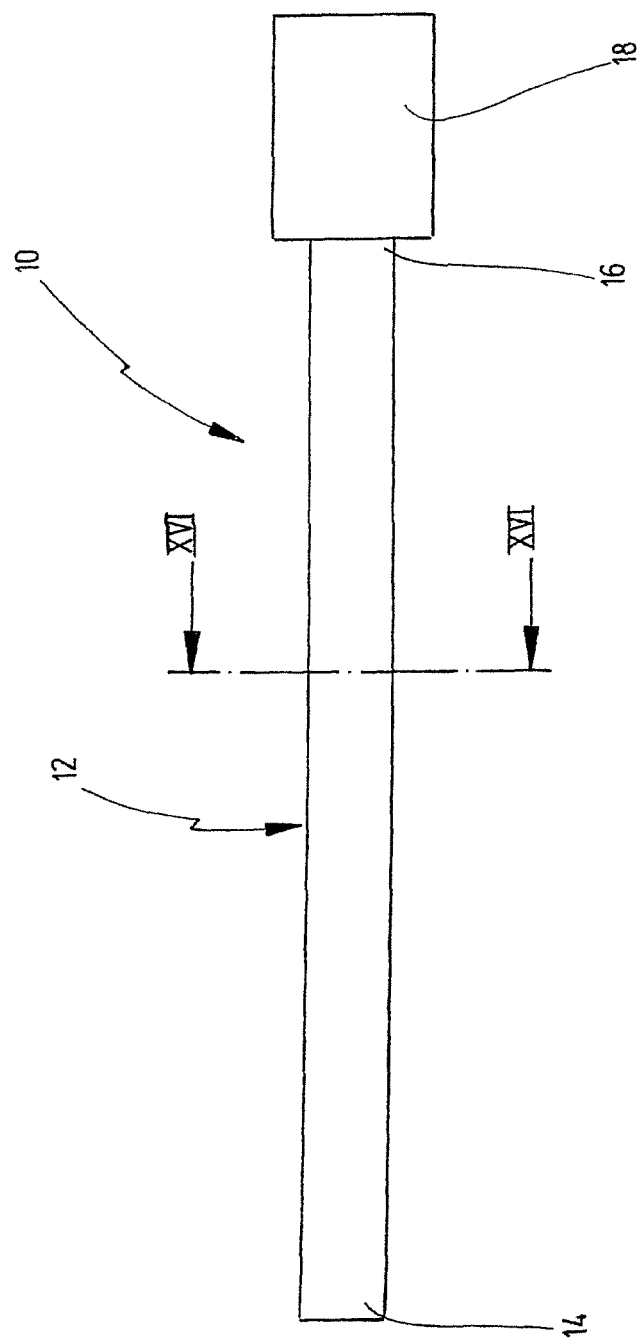
FIG. 14 shows a schematic side view of an optical medical instrument according to a further illustrative embodiment.

First of all, FIG. 14 is a schematic representation of the optical medical instrument 10, with the elongate shaft 12 between the distal end 14 and the proximal end 16 and the instrument head housing 18.

Figure 15:
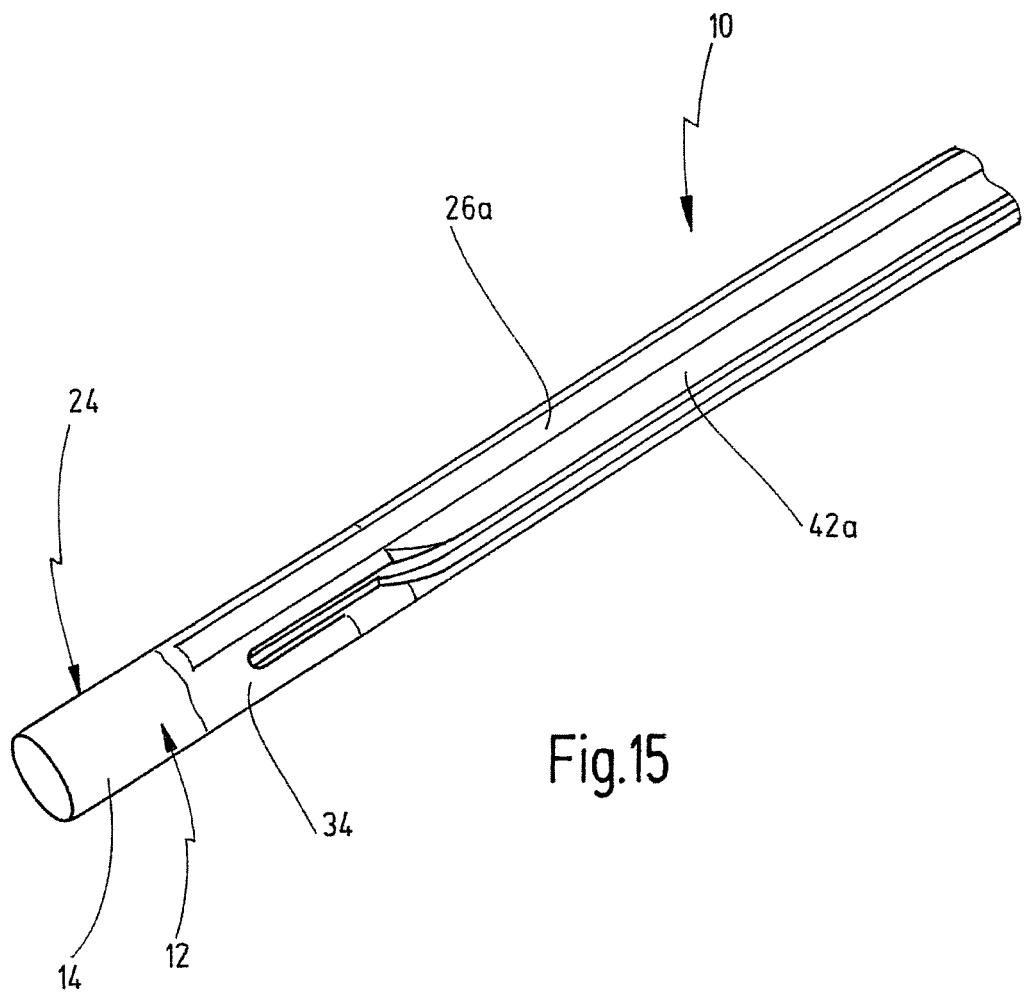
FIG. 15 shows a part of the instrument from FIG. 14 with the shaft in partial section.

The instrument 10 is shown cut away in FIG. 15, wherein the shaft 12 is also broken open along quite a large part of its longitudinal extent. The heat source 24 is located in the distal end area of the shaft 12. The first heat pipe 26a, the heat coupling element 34 and the heat sink body 42a can be seen in FIG. 15.

Figure 16:
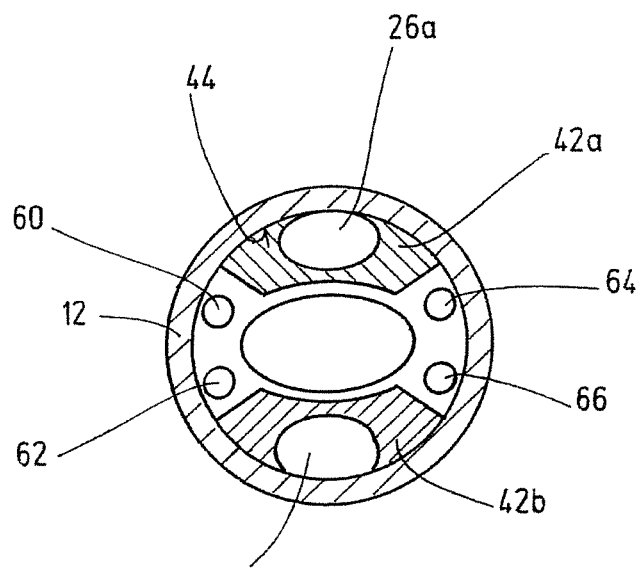
FIG. 16 shows a section through the instrument from FIG. 14 along a line XVI-XVI in FIG. 14 and on an enlarged scale in relation to FIG. 14.

FIG. 16 shows a cross section through the arrangement in FIG. 15, in a section along the line XVI-XVI in FIG. 14. In the section according to FIG. 16, the second heat pipe 26b and the second heat sink body 42b can also be seen. In the illustrative embodiment according to FIGS. 15 and 16, the heat pipes 26a and 26b are each in direct thermally conductive form-fit contact with the inner face 44 of the shaft 12, and, furthermore, the two heat pipes 26a and 26b are connected with a form fit to the respective heat sink body 42a and 42b. The heat pipes 26a and 26b are pressed into the heat sink bodies 42a and 42b, as a result of which the form-fit engagement is obtained. By pressing in the heat pipes 26a and 26b, the latter are slightly deformed in cross section, as is shown in FIG. 16. As is likewise shown in FIG. 16, the heat sink bodies 42a and 42b extend along the inner face 44 of the shaft 12 only about a part of the circumference, such that areas remain free in the shaft 12 between the heat sink bodies 42a and 42b and can be used for the passage of current-carrying lines, light-carrying lines or the like, as is indicated by 60, 62, 64 and 66.

Figure 17:
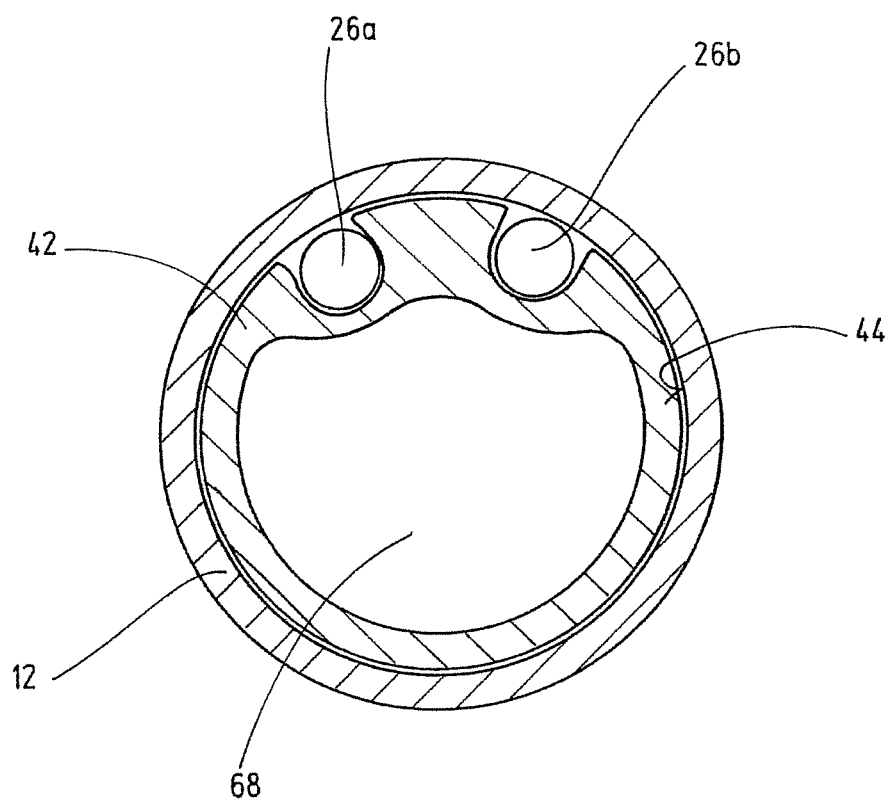
FIG. 17 shows a section similar to FIG. 16 through a shaft of an optical medical instrument according to a further illustrative embodiment.

FIG. 17 shows an alternative to FIG. 16 as regards the design and arrangement of the two heat pipes 26a and 26b, and also of the heat sink body 42 which, in this illustrative embodiment, is formed about the entire circumference. In this illustrative embodiment in FIG. 17, the heat pipes 26a and 26b are again in direct contact with the inner face 44 of the shaft 12 about part of the circumference, and the heat pipes 26a and 26b are otherwise connected thermally conductively, and with a form fit, to the heat sink body 42. The heat sink body 42 couples the heat pipes 26a and 26b to the inner face 44 of the shaft 12 about the entire circumference.

The heat sink body 42 encloses an inner area 68, which can be used for the routing of lines. In this illustrative embodiment, the heat pipes 26a and 26b are not pressed into the heat sink body but instead merely inserted and therefore not deformed in cross section.

It will be appreciated that the aspects described with reference to the illustrative embodiments in FIGS. 1 to 13 may also be used in the illustrative embodiments in FIGS. 14 to 17, and vice versa.

What is claimed is:

1. An optical medical instrument, comprising:
an elongate tubular shaft;
a heat source generating lost heat during use of the optical medical instrument; and
a heat pipe extending inside the shaft in a longitudinal direction of the shaft and having a distal heat pipe end and a proximal heat pipe end, the heat pipe being thermally coupled to the heat source in order to collect the lost heat from the heat source and to remove the lost heat from the heat source;
wherein the heat pipe is coupled thermally conductively and two-dimensionally to the shaft between the distal heat pipe end and the proximal heat pipe end over at least a partial length of the heat pipe and over at least a partial circumference of the heat pipe, in order to remove the lost heat from the heat pipe, over at least a partial length and over at least a partial circumference of the shaft, to an environment of the optical medical instrument; and
wherein the heat pipe extends over at least half the length of the shaft and is coupled thermally conductively to the shaft over at least half the length of the shaft.

2. The instrument of claim 1, wherein the heat pipe is coupled thermally conductively to the shaft over at least half the total length of the heat pipe.

3. The instrument of claim 1, wherein the heat pipe is coupled thermally conductively to the shaft almost or completely over the total length of the heat pipe.

4. The instrument of claim 1, wherein the heat pipe is thermally coupled at least in part directly to the shaft, wherein the heat pipe is in contact with an inner face of the shaft at least over part of the circumference.

5. The instrument of claim 4, wherein the heat pipe is in contact with the inner face of the shaft with a form fit.

6. The instrument of claim 1, wherein the heat pipe is coupled thermally conductively to the shaft over at least part of the circumference via a heat sink body, wherein the heat sink body is in form-fit contact with the heat pipe and with an inner face of the shaft, in each case over at least part of the circumference.

7. The instrument of claim 1, wherein the heat pipe is coupled thermally conductively to the shaft section-wise via a plurality of heat sink bodies, wherein the heat sink bodies are distributed along the heat pipe.

8. The instrument of claim 1, wherein the heat pipe is connected to the heat source via a thermally conductive heat coupling element.

9. The instrument of claim 8, wherein the heat pipe is connected to the thermally conductive heat coupling element with a form fit.

10. The instrument of claim 8, wherein the heat pipe is pressed into the heat coupling element.

11. The instrument of claim 8, wherein the heat pipe is additionally fixed in or on the heat coupling element via a thermally conductive joining agent.

12. The instrument of claim 8, wherein the heat coupling element is designed as a thermally conductive bearing with at least one degree of freedom of movement with respect to the heat source.

13. The instrument of claim 1, wherein the heat source is arranged in at least one of: a distal end area of the shaft, in a middle portion of the shaft, in a proximal end area of the shaft.

14. The instrument of claim 13, wherein the heat pipe is thermally coupled to the heat source via at least one of: the distal heat pipe end, a middle portion between the distal heat pipe end, the proximal heat pipe end, or via the proximal heat pipe end.

15. The instrument of claim 1, wherein the heat source is a first heat source, and at least one second heat source is located at a distance from the first heat source in the longitudinal direction of the shaft, wherein the heat pipe is thermally coupled to the first heat source and the at least one second heat source.

16. The instrument of claim 1, wherein the heat pipe has a first heat pipe and at least one second heat pipe, wherein at least one of the first heat pipe and the at least one second heat pipe is thermally coupled to the heat source.

17. The instrument of claim 1, wherein the heat pipe is a sintered heat pipe.

18. The instrument of claim 1, wherein the instrument is an endoscope.

19. The instrument of claim 1, wherein the instrument is an exoscope.

20. The instrument of claim 1, further comprising an instrument head housing; and
wherein the shaft extends from the instrument head housing.

* * * * *